United States Patent
Cornil

(10) Patent No.: US 8,449,587 B2
(45) Date of Patent: May 28, 2013

(54) SKIN WOUND TREATMENT SYSTEM, DRESSING AND BIOCHEMICAL ACTIVATION DEVICE FOR THE USE OF SUCH A SYSTEM

(75) Inventor: Alain Cornil, Aix-en-Provence (FR)

(73) Assignee: Vivatech Company, Paris (FR)

( * ) Notice: Subject to any disclaimer, the term of this patent is extended or adjusted under 35 U.S.C. 154(b) by 200 days.

(21) Appl. No.: 12/087,434

(22) PCT Filed: Nov. 6, 2006

(86) PCT No.: PCT/FR2006/002462
§ 371 (c)(1),
(2), (4) Date: Jul. 2, 2008

(87) PCT Pub. No.: WO2007/080239
PCT Pub. Date: Jul. 19, 2007

(65) Prior Publication Data
US 2009/0062718 A1   Mar. 5, 2009

(30) Foreign Application Priority Data
Jan. 9, 2006 (FR) ...................................... 06 00160

(51) Int. Cl.
*A61N 5/067* (2006.01)
(52) U.S. Cl.
USPC ................................... 607/89; 607/88; 606/9
(58) Field of Classification Search
USPC ...................... 606/9–14, 214–216; 607/88–91
See application file for complete search history.

(56) References Cited

U.S. PATENT DOCUMENTS

| | | | |
|---|---|---|---|
| 5,156,613 A | 10/1992 | Sawyer et al. | |
| 6,032,062 A | 2/2000 | Nisch | |
| 6,074,382 A * | 6/2000 | Asah et al. | 606/9 |
| 6,334,069 B1 * | 12/2001 | George et al. | 607/2 |
| 6,773,699 B1 * | 8/2004 | Soltz et al. | 424/78.03 |
| 7,307,530 B2 * | 12/2007 | Fabian et al. | 340/572.1 |

FOREIGN PATENT DOCUMENTS

| | | |
|---|---|---|
| FR | 2 598 088 | 11/1987 |
| WO | WO 97/17025 | 5/1997 |

OTHER PUBLICATIONS

International Search Report for PCT/FR2006/002462 dated of completion Mar. 28, 2007.
Amendment and Response to the Jan. 31, 2012 Office Action for U.S. Appl. No. 12/227,882 (10 pgs.).
Non-Final Office Action date mailed Jan. 31, 2012 for U.S. Appl. No. 12/227,882 (12 pgs.).

* cited by examiner

*Primary Examiner* — Ahmed Farah
(74) *Attorney, Agent, or Firm* — Mintz Levin Cohn Ferris Glovsky and Popeo, P.C.

(57) ABSTRACT

The present invention relates to a system for treatment of skin wounds, comprising an energy source for activation of a biochemical healing effect, and at least one dressing intended to be placed on the wound before the step of activation by said energy source, characterized in that said dressing comprises an identification means interacting in a contactless manner with a sensor that triggers the function of the energy source only when the distance between the sensor and said identification means is below a threshold value.

2 Claims, 1 Drawing Sheet

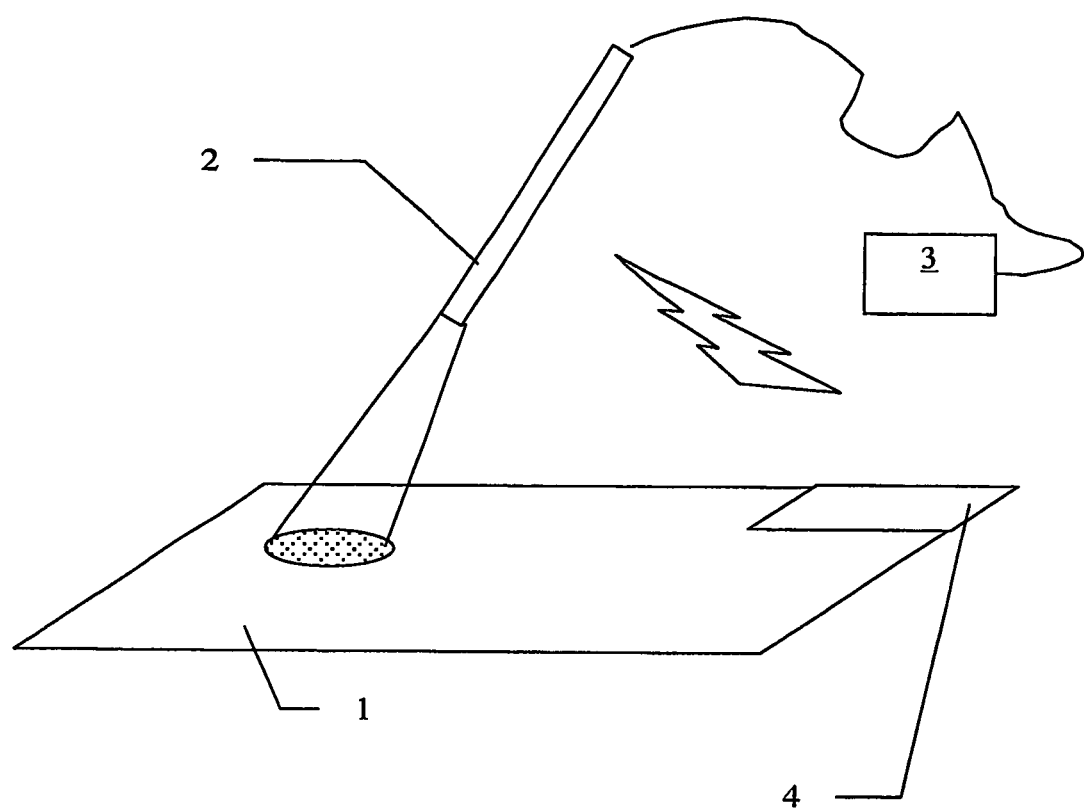

SKIN WOUND TREATMENT SYSTEM, DRESSING AND BIOCHEMICAL ACTIVATION DEVICE FOR THE USE OF SUCH A SYSTEM

CROSS REFERENCE TO RELATED APPLICATIONS

This application claims benefit to PCT Application No. PCT/FR2006/002462, having an international filing date of Nov. 6, 2006, which claims priority to French patent application no. 06/00160, filed Jan. 9, 2006. Each of the foregoing disclosures is expressly incorporated herein by reference in its entirety.

The present invention relates to the repair of skin wounds.

Various solutions are known in the prior art, consisting of improving the suture and healing process by using an external energy source. The lips of the wound are brought together and held in place by a dressing, which may include active ingredients that are activatable by the external energy source.

International patent application WO9717025 describes a treatment process consisting of affixing a cross-linked material containing a non-collagenous protein component onto a tissue. This cross-linked material is first placed on a target location on the tissue, and energy is then applied to the cross-linked material. The non-collagenous protein component is such that when energy is applied in an appropriate quantity, the matrix adheres to the tissue.

European patent application EP265470 describes a device for uniting the lips of a wound, comprising a laser whose emission wavelength is chosen such that it can perform tissue bonding and unite the lips of the wound, and a holding piece suitable for being secured to the tissue around the wound so as to hold the lips of said wound in contact, at least while the wound is exposed to said laser radiation. The holding piece includes at least one region suitable for being positioned over the wound and sufficiently transparent at the wavelength of laser radiation for the energy of said radiation to be sufficient, after it has passed through said region, to perform the desired tissue bonding.

Use of activation devices such as a laser source is not without danger and handling such apparatus may cause accidents if the beam is inadvertently directed towards the eye of a person present in the operating area.

The aim of the present invention is to avoid such disadvantages in the prior art.

To this end, in its most general form, the invention relates to a skin wound treatment system comprising an energy source for activating a biochemical wound-healing effect and at least one dressing designed to be affixed to the wound before the activation stage is performed using said energy source, characterised in that said dressing includes an identification means that interacts without contact with a sensor that controls the operation of the energy source only when the distance between the sensor and said identification means is less than a threshold value.

Preferably, the detection distance of the identification means is below fifty centimeters.

In a preferred variant, the energy source consists of a laser source.

In a first embodiment, the identification means consists of at least one permanent magnet and is characterised in that the sensor in the device is a magnetic sensor associated with a calculator to calculate a distance according to the electromagnetic signals detected.

In a second embodiment, the identification means consists of optical markings and is characterised in that the sensor in the device is an image detector associated with a calculator to calculate a distance according to the image detected.

In a preferred embodiment, the identification means consists of a transponder.

Advantageously, the identification means includes a unique identifier for the dressing model associated with it.

Preferably, the operating settings of the energy source are controlled according to said unique identifier.

The invention also provides a dressing for use with such a system, characterised in that it includes an identification means, and additionally a biochemical activation device that includes an energy source controlled by a calculator that receives a signal from a sensor suitable for interacting with the identification means incorporated in a dressing.

The invention will best be understood by reading the following description and referring to the appended illustration, which provides a schematic view of a device as claimed by the invention.

The dressing (1) is formed by a transparent film as described in European patent application EP265470. It woks in cooperation with a handpiece (2), which includes a laser source, controlled by a control unit (3) that supplies power to and controls the laser source.

Dressing (1) includes a radio frequency identification (RFID) tag (4). This tag includes in a known manner an induction loop providing power supply to a circuit that includes a memory in which a dressing type identifier is recorded.

This information can be used to optimise the settings of the associated energy source, in particular the power, duration and frequency of the pulses.

The handpiece (2) that includes the laser has a power supply that can activate tag (4) by means of an electromagnetic field detected by the induction loop. It also includes a sensor designed to receive electromagnetic signals emitted by RFID tag (4) when the latter is supplied with power.

Activation of the laser depends on the detection of an identification signal from a tag. If such a signal is not detected, the laser is on standby and thus prevents any risk of accident, even when inadvertently directed towards a person.

In particular, when handpiece (2) is at a distance from the dressing that is greater than the range of RFID tag (4), the laser is inactive.

The different laser control settings, according to the different types of dressing, are recorded in the memory of the laser control unit, for instance in the form of a table. These settings may be updated, particularly in the event that a new type of dressing is marketed, via a link with an external computerised device, or by data entry using an input interface incorporated in control unit (3).

The invention is not limited to an interaction between an RFID tag and a sensor.

In an equivalent variant, the interaction may take place via magnetic markers affixed to the dressing. These markers comprise thin magnet items or magnetised particles. In this case, the handpiece includes one or more magnetosensitive sensors, for instance Hall effect sensors, which output a signal according to the field amplitude detected in one or more directions. These signals are used by a calculator to determine the distance and direction of the magnetic markers affixed on the dressing, by a known method of triangulation.

In another equivalent variant, the interaction may take place by affixing an optical marking, for instance a fluorescent marking, that is excited by a secondary source fitted in the handpiece. The handpiece in this case includes an optical sensor, for instance a sensor including a CCD (charge-coupled device) associated with a calculator that analyses the image detected in order to calculate the distance and possibly the direction of the marking on the dressing from the handpiece. This marking may take the form of a matrix code or geometrical figures by which the distance may be deduced on the basis of the size and deformation of the image, as detected by the sensor in the handpiece.

The dressing may consist of a simple transparent film, by which the lips of the wounds are brought together and temporarily held in place and through which the energy provided by the handpiece can be transferred.

It may also include active coatings involved in the biochemical reactions under the effect of excitation by an energy source.

The energy source described is a laser beam. However, other equivalent energy sources such as ultrasound, radio-frequency electromagnetic waves or a thermal source may be used and would constitute a technical equivalent. Nevertheless, a laser source remains the preferred solution.

The invention claimed is:

1. A skin wound treatment system comprising:
   a handpiece including a pulsed laser source for activating a biochemical wound-healing effect controlled by a calculator that receives a signal from a sensor; and
   at least one dressing for affixation to a wound before activation of the laser source; wherein:
   the dressing includes an identification means corresponding to a radio frequency identification (RFID) tag comprising an induction loop that interacts without contact and without electrical connection with the sensor;
   the handpiece has a power supply generating an electromagnetic field that can activate the RFID tag, by detecting an electromagnetic field generated by the induction loop of the RFID tag,
   the induction loop provides power to a circuit that includes a memory in which a dressing type identifier is recorded, the information being used to control the power, the duration and the frequency of the pulses of the laser source; and
   the sensor enables operation of the laser source upon the distance between the sensor and the identification means being less than a determined threshold value and the sensor is configured to receive electromagnetic signals emitted by RFID tag corresponding to the stored information when the latter is supplied with power so as to control the power, the duration and the frequency of the pulses of the laser source.

2. A wound treatment system as claimed in claim 1, wherein:
   the identification means comprises at least one permanent magnet,
   the sensor comprises a magnetic sensor,
   and the calculator calculates a distance according to the electromagnetic signals detected.

* * * * *